United States Patent
Gural et al.

(10) Patent No.: US 7,022,290 B2
(45) Date of Patent: Apr. 4, 2006

(54) SYSTEM STRUCTURE FOR IN SITU X-RAY STUDY OF ELECTROCHEMICAL CELL COMPONENT PERFORMANCE

(75) Inventors: John Gural, Fords, NJ (US);
Jean-Bernard Leriche, Boves (FR);
Mathieu Morcrette, Amiens (FR);
Jean-Marie Tarascon, Amiens (FR)

(73) Assignee: Rutgers, the State University, New Brunswick, NJ (US)

( * ) Notice: Subject to any disclaimer, the term of this patent is extended or adjusted under 35 U.S.C. 154(b) by 560 days.

(21) Appl. No.: 09/884,283

(22) Filed: Jun. 19, 2001

(65) Prior Publication Data

US 2002/0192121 A1 Dec. 19, 2002

(51) Int. Cl.
*B01L 9/00* (2006.01)
*B01L 3/00* (2006.01)
*B01L 11/00* (2006.01)
*H01M 8/00* (2006.01)
*H01M 10/00* (2006.01)

(52) U.S. Cl. ............... 422/104; 422/102; 422/103; 204/193; 204/194; 204/400; 429/12; 429/48; 429/50; 429/57; 429/96; 429/121; 429/122

(58) Field of Classification Search ........... 422/102, 422/103, 104; 204/193, 194, 400; 429/12, 429/48, 50, 57, 96, 121, 122
See application file for complete search history.

(56) References Cited

U.S. PATENT DOCUMENTS

| | | | | |
|---|---|---|---|---|
| 3,201,278 A | * | 8/1965 | Kurtzweil et al. | 429/112 |
| 3,867,201 A | * | 2/1975 | Holmes | 429/118 |
| 4,186,246 A | * | 1/1980 | Sugalski | 429/60 |
| 5,110,696 A | | 5/1992 | Shokoohi et al. | |
| 5,196,279 A | * | 3/1993 | Tarascon | 429/338 |
| 5,415,957 A | * | 5/1995 | Okada et al. | 429/330 |
| 5,635,138 A | * | 6/1997 | Amatucci et al. | 422/104 |
| 5,911,947 A | * | 6/1999 | Mitchell | 29/623.2 |
| 6,413,667 B1 | * | 7/2002 | Gozdz | 429/62 |

* cited by examiner

*Primary Examiner*—Jill Warden
*Assistant Examiner*—Brian Sines
(74) *Attorney, Agent, or Firm*—Lowenstein Sandler PC

(57) ABSTRACT

A structural system for accurately reproducible in situ x-ray studies of operating rechargeable electrochemical battery cell electrode components comprises an hermetically sealed cell component enclosure incorporating an x-ray transmissive window member of beryllium or the like. A research embodiment of the system comprises means for rapidly and consistently interchanging electrode compositions for operative comparison and evaluation, while a laminated cell system embodiment enables accurate testing of electrode components in commercial configurations such as unitary polymeric Li-ion battery cells.

3 Claims, 2 Drawing Sheets

SYSTEM STRUCTURE FOR IN SITU X-RAY STUDY OF ELECTROCHEMICAL CELL COMPONENT PERFORMANCE

BACKGROUND OF THE INVENTION

The present invention relates to rechargeable electrochemical energy storage systems, and particularly relates to means for studying the operative structure and phase changes occurring within such systems comprising rechargeable cells of complementary electrodes capable of reversibly intercalating, alloying, or otherwise alternately combining with and releasing mobile ions of, e.g., sodium, potassium, or preferably lithium, in electrical energy charge and discharge operations. The invention relates, more particularly, to a rechargeable energy storage cell structure system which may be readily and reproducibly fabricated and which incorporate means for in situ study, typically under incident x-radiation, of operating cell electrode components.

The present invention in essence represents an improvement on an earlier apparatus, described in U.S. Pat. No. 5,635,138, the disclosure of which is incorporated herein by reference, for in situ x-ray study of rechargeable electrochemical cells. In that prior system, an apparatus was provided for holding, in operative relation to the transmissive window of an x-ray diffraction apparatus, a fabricated cell usually comprising a laminated assembly of positive and negative electrode members having an intervening ion-conductive, electrically insulating separator member which provided an ion-mobilizing electrolyte medium. The cell assembly commonly also comprised interlayered current collector members which provided conductive electrical connections for utilization of the cell.

Although the prior apparatus and the method of its application provided sufficiently reliable test results for the evaluation of a single cell then under examination, the extensive manipulation of cell members during the required assembly and lamination of multiple test cells, as well as the alignment of apparatus elements, contributed to an inordinate expense of time and represented a source of unpredictable test parameter variations. These disadvantages were particularly notable, for example, in the oft-practiced comparative testing of series of cells varying in minor electrode component ratio adjustments. Such lack of consistent and precisely reproducible cell assembly and test conditions have led to significant difficulties in optimizing compositions for commercial rechargeable electrochemical cells.

The present invention, on the other hand, provides a combination of proven electrochemical cell assembly and fabrication means with an x-ray capable examination component to yield a rapidly implemented, consistently reproducible test cell system. In a preferred research embodiment, this system utilizes a cell assembly comprising a conventional, widely employed Swagelok electrochemical test cell device, such as that described, for example, in U.S. Pat. Nos. 5,110,696 and 5,196,279, in combination with an x-ray transmissive cell window component of beryllium, or the like, which serves as part of an integrated hermetic enclosure for an operative rechargeable electrochemical cell. The fixed physical relationship of cell components and the ready manipulation of cell assembly members ensures rapid and economical fabrication of consistent test cells, as well as reproducible examination test results.

SUMMARY OF THE INVENTION

The structure of the electrochemical cell in situ x-ray study system of the present invention combines, in a preferred embodiment, the basic cylinder and piston cell assembly components of a conventional Swagelok test cell with an x-ray transmissive beryllium window member and integral hermetic sealing means which combine to serve as a complementary closure of the cell. Active electrode and separator members of a test cell may be quickly assembled, in the usual manner, within the cylinder space of the cell and activated by the addition of electrolyte prior to the usual sealing with the piston/terminal member. Insulative lining within the cell cylinder electrically isolates the active cell electrodes, thus eliminating the aspect of the above-noted prior device which required the inconvenient electrical isolation of the main body members of that device. In the present structure, the spatial relationship between the electrochemically active cell members and the beryllium viewing window is advantageously fixed among all cells in a test series by virtue of the window's constituting the same integral sealing member of each such cell.

In another embodiment of the invention an x-ray transmissive viewing window comprises a section of the hermetic sealing envelope enclosure of a conventional laminated polymeric layer member cell structure, such as commonly employed in rechargeable Li-ion battery cells. While adapted more for studying final optimization configurations of such battery cells than for rapid research component or composition interchange, such an embodiment nonetheless ensures reliable and reproducible operative results in commercial battery fabrications.

BRIEF DESCRIPTION OF THE DRAWING

The present invention will be described with reference to the accompanying drawing of which.

DESCRIPTION OF THE INVENTION

Figure 1:
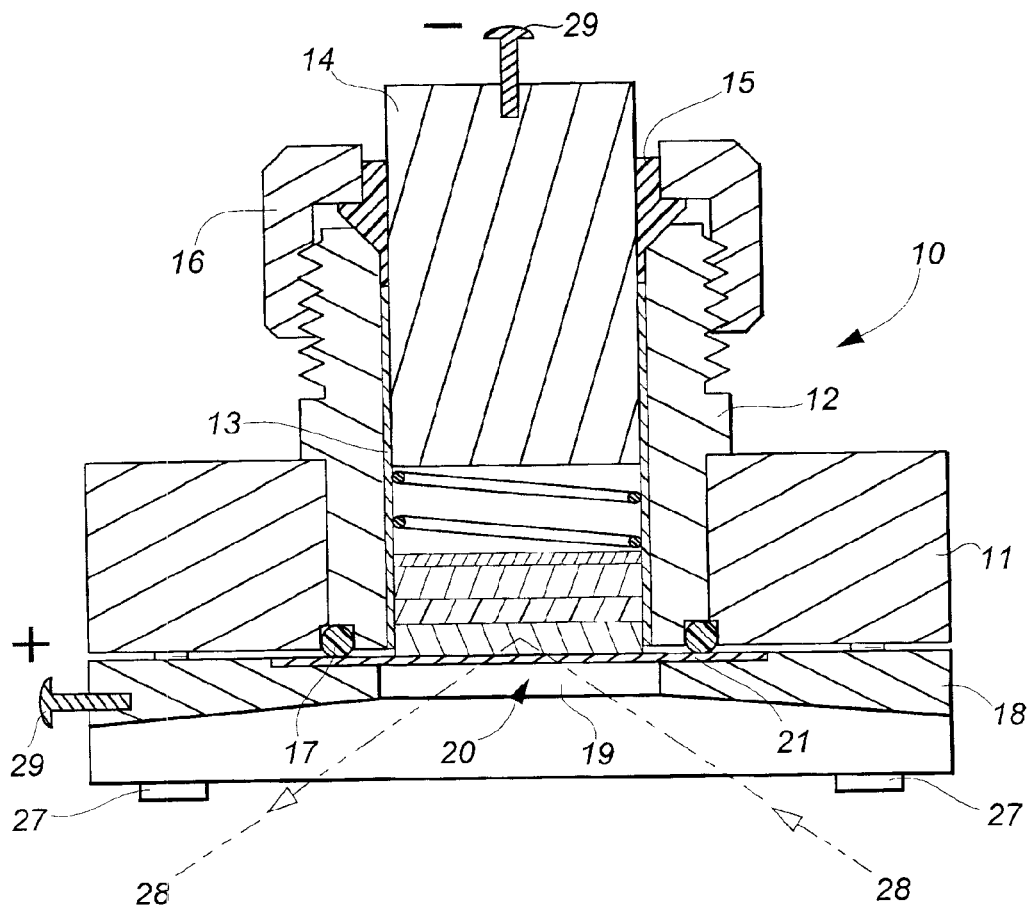
FIG. 1 depicts in cross-section elevation an electrochemical research cell system structure embodying the present invention.

As shown in FIG. 1, an embodiment of the electrochemical cell in situ x-ray study system according to the present invention comprises a body 10, typically of stainless steel components, comprising a body block 11 into which is fixed, such as by means of press fit dimensioning, a body cylinder member 12. Cylinder member 12 is similar in function to the cylinder member of a conventional Swagelok electrochemical test cell device and is likewise threaded at its distal end to receive a threaded collar 16. Surrounding the proximal end of the cylinder opening of body 10 is cell sealing means, such as an O-ring 17 set into a circular receiving channel in body 10. The cell further comprises a base plate member 18 which comprises a through opening 19 providing access of incident x-radiation to the interior of the body cylinder. Base member 18 is otherwise typically sized and shaped for mounting in the usual manner upon a selected commercial x-ray diffraction test apparatus.

Assembling an electrochemical cell for test in the present system embodiment entails situating a window member 21, typically of beryllium and set in a receiving recess in base plate member 18, coextensive with base plate opening 19, aligning the proximal cylinder opening of body 10 with sealing means 17 surrounding opening 19 and in contact with window 21, and joining body block 11 to base plate 18 by means of bolts 27 to thereby form an hermetic seal between window 21 and sealing means 17 at the proximal end of the body cylinder. In order to prevent later short circuiting of the active cell electrode members, a sleeve 13 of electrically insulating material, such as polyethylene terephthalate, may be situated within the body cylinder to cover at least that portion of the interior wall of the cylinder which could otherwise contact electrically conductive members of the cell.

Figure 2:
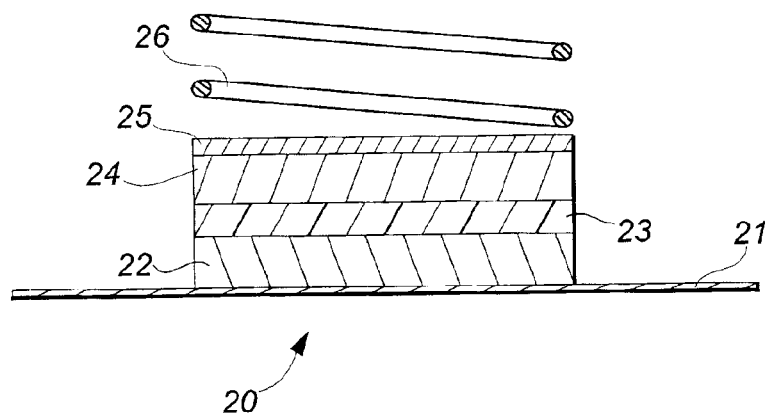
FIG. 2 presents an enlarged view of a segment of FIG. 1 depicting in greater detail active electrode cell members.

The active electrode and separator members of the cell, shown generally at 20 in FIG. 1 and depicted in greater detail in FIG. 2, are then inserted into the distal cylinder opening of body 10 to contact window 21. In a cell structured, for example, to examine the operation of active positive electrode material, such an electrode member 22, sized to cylinder cross-section dimensions from a desired composition layer, is positioned within the body cylinder in electrical contact with window 21. In certain high-voltage test procedures, an alternative component arrangement (not shown) may include a radiation-transparent, insulative film disposed between electrode 22 and window 21, and an intra-electrode conductor element providing electrical communication between electrode 22 and body 10. A separator member 23 of common ion-transmissive, electrically insulative material is positioned within the body cylinder in contact with electrode member 22, and a complementary electrode member 24 of active negative electrode material is placed in contact with separator member 23. For examination of a negative cell electrode material, locations of electrode members 22, 24 are simply transposed in the cell assembly.

When implementation of the test cell is to commence, an activating measure of desired electrolyte solution, typically comprising a non-aqueous solvent and a dissociable salt of the mobile cation of the active cell system, e.g., lithium, is introduced into the cylinder to contact and substantially saturate the electrode/separator assembly. A pressure disc 25 of stainless steel is positioned on electrode member 24 in order to uniformly distribute to the electrode assembly the compressive force applied through spring 26 by the subsequent insertion of piston member 14. Such insertion of piston member 14 is made through slidable engagement with electrically insulating compression ring member 15 of polypropylene or the like situated in the distal end of body cylinder member 12. When the desired degree of pressure has been applied to the electrode assembly, the position of piston 14 is fixed by threadedly tightening collar 16 upon ring 15 to simultaneously compress the ring and hermetically seal the distal end of the cell cylinder.

Subsequent to the mounting of the activated cell upon a selected x-ray diffraction apparatus, operation of the cell is initiated by appropriate electrical charge or discharge through conductors communicating between commercial control and recording test apparatus, e.g., a BioLogic MacPile galvanostat, not shown, and cell terminal studs 29. During such operation, test apparatus x-ray radiation 28—28 is directed through window 21 and into electrode layer 22 in order to determine, for example, phase variations occurring within the electrode composition during cycling intercalation of mobile Li ions.

A significant advantage provided by the test cell structure of the present system is apparent in the simplicity of cell assemblage and the rapid manner in which series of varying electrode compositions may be interchanged for nearly continuous examination and test. Disassembly of a given tested cell, removal of used components, cleaning of the interior cell space, insertion of electrodes of varying composition, activation of new cell assembly, and cell structure sealing for test operation may all be accomplished within minutes and with reliable assurance that each successive test procedure will be conducted under substantially identical cell structure conditions.

Figure 3:
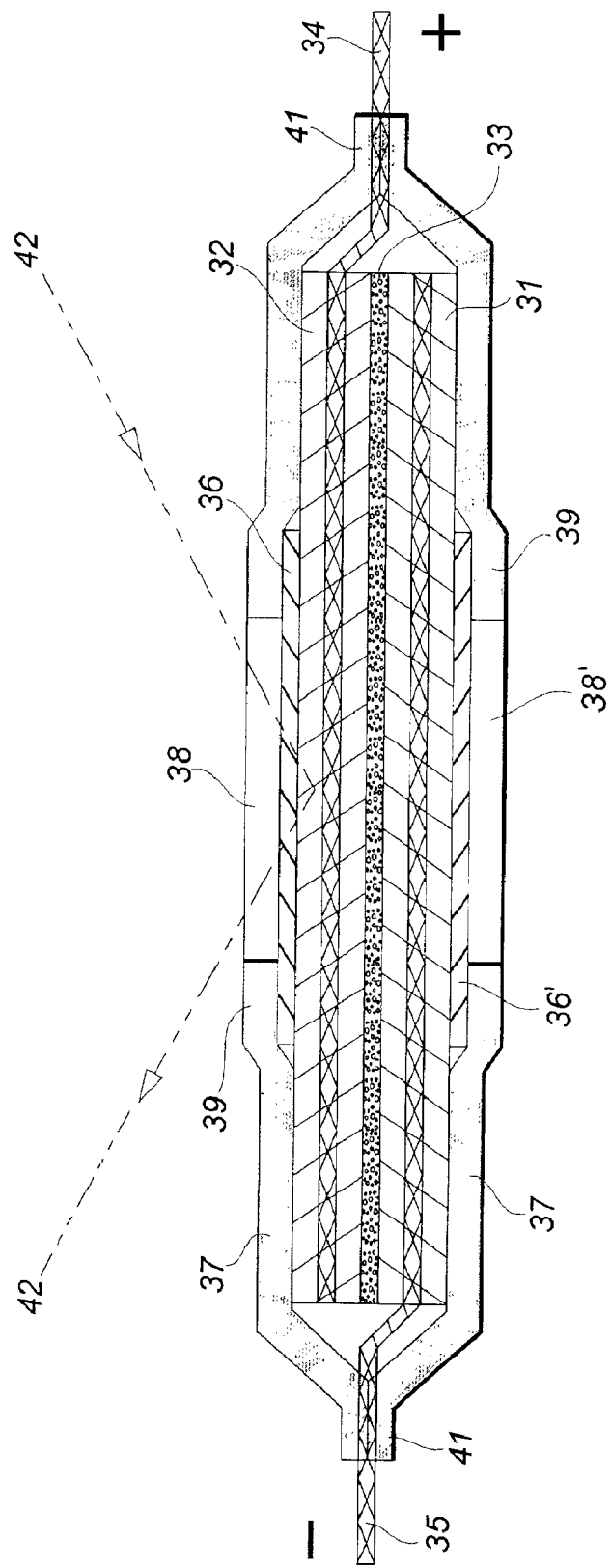
FIG. 3 depicts in cross-section elevation a laminated rechargeable electrochemical lithium-ion battery cell system structure embodying the present invention.

A system structure according to present invention may also be employed in a configuration depicted in the embodiment of FIG. 3 to evaluate in x-ray diffraction studies compositions and components of increasingly popular laminated polymeric rechargeable electrochemical cells, e.g., Li-ion secondary battery cells. As with the cell embodiment of FIG. 1, this embodiment provides consistent test cell component relationships through the incorporation of an x-ray scan window as an integral part of the cell containment assembly.

As shown in FIG. 3, such an electrochemical test cell system comprises a negative electrode member 31, a positive electrode member 32, and an interposed electrically insulative, ion-conductive separator member 33, each typically comprising respective polymer compositions of active electrochemical materials and electrolyte absorbing configuration, laminated to form a unitary secondary battery assembly. Also included in this assembly are electrically conductive current collector members 34, 35, often in the form of reticulated metallic mesh structure laminated within the body of their associated electrode member layers, which provide means for application and withdrawal of cycling electrical current to and from the cell. Such selection and disposition of these collector materials advantageously provide porosity for penetration of later-applied electrolyte and allow unhindered incidence of x-radiation into the electrode compositions layers under investigation.

Hermetic enclosure of the laminated electrode assembly to protect and retain electrolyte solution within the cell is effected by enveloping polymeric sheet material 37 which preferably is adapted for thermoadhesive sealing. A pair of appropriately sized such sheets 37 are provided with x-ray access opening 38 and concentrically situated beryllium window 36, hermetically sealed to sheet 37 in peripheral region 39, located to overly the examination site of electrode member 32 when sheets 37 are arranged to encompass the laminated cell assembly. When it is desired to study the performance of both electrode members 31, 32, optional access opening 38' and window 36' may be added to the cell system structure.

Prior to commencement of a cell test, a measure of electrolyte is introduced to the laminated electrode assembly, and the peripheral overlapping regions of the encompassing sheets 37, 37 are thermally adhered, as at 41, to hermetically seal the electrochemical cell structure. The extensions of collector members 34, 35 beyond seal regions 41 provide terminal connections for implementation of electrical control and recording apparatus. The completed test cell system comprising sealed window member 36 may be mounted in any convenient manner upon x-ray diffraction apparatus in the incident path of x-radiation 42, 42 during charge/recharge cycling in order to observe the performance of active composition in electrode 32.

When anticipated test voltage levels are expected to increase to a range approaching about 5 V, a protective, transparent film (not shown) of polyethylene terephthalate or the like may be interposed between positive electrode 32 and window 36 in order to obviate electrochemical erosion of that window. In a further alternative configuration, polymeric enclosure sheets 37, 37 may be preformed, with sealed window member 36 and thermoadhesive closure about a significant portion of sheet periphery, into an open-ended envelope to receive a laminated cell and activating electrolyte. Electrode members of such a cell would preferably be assembled with associated collector members 34, 35 extending in parallel from a single edge of the laminated structure to facilitate extension through the single envelope access prior to final peripheral hermetic sealing.

It is anticipated that other embodiments and variations of the present invention will become readily apparent to the skilled artisan in the light of the foregoing description, and such embodiments and variations are intended to likewise be included within the scope of the invention as set out in the appended claims.

What is claimed is:

1. A system for in situ x-ray study of electrode component performance in a rechargeable electrochemical energy storage cell comprising a combination of opposed polarity electrode members and interposed separator member with electrolyte disposed within a hermetic enclosure having an integral x-ray transmissive window member situated to allow incidence therethrough of such radiation upon an electrode member site under study characterized in that the system comprises:

a) a body providing a cylinder for receiving therein components of said cell member combination;
b) sealing means surrounding the proximal end of said cylinder;
c) a base plate providing a radiation access opening situated adjacent said cylinder proximal end and aligned concentrically therewith and within the circumference of said sealing means;
d) said window member being situated intermediate said base plate and said sealing means and extending peripherally beyond said sealing means;
e) means for removably affixing said base plate to said body and compressing said sealing means against said window to form an hermetic seal therewith;
f) adjustable means situated at the distal end of said cylinder for applying compressive force urging said combination of cell components within said cylinder toward contact with said window member; and
g) means for hermetically sealing said cylinder distal end.

2. A system according to claim 1 wherein:

a) said body, said base plate, and said electrode member under study are in electrical continuity;
b) said adjustable means comprises an electrically conductive piston member axially displaceable within said cylinder and in electrical continuity with the electrode member of opposed polarity to said electrode member under study; and
c) said cylinder distal end sealing means comprises an electrically insulating ring member fitted to the annular space between said piston member and said cylinder distal end and compressible therein to mechanically fix the axial displacement of said piston member and effect said distal end hermetic seal while electrically insulating said piston from said body.

3. A system according to claim 2 wherein means situated within the annular space between said piston member and the interior wall of said cylinder electrically insulates said body from cell member components in electrical continuity with said piston.

* * * * *